(12) United States Patent
Robinson et al.

(10) Patent No.: US 9,962,404 B2
(45) Date of Patent: May 8, 2018

(54) CELL FOR ELECTROLYZING A LIQUID

(71) Applicant: Reoxcyn Innovation Group, LLC, Pleasant Grove, UT (US)

(72) Inventors: Daniel Robinson, Salt Lake City, UT (US); James Pack, Salt Lake City, UT (US)

(73) Assignee: Reoxcyn Innovation Group, LLC, Pleasant Grove, UT (US)

( * ) Notice: Subject to any disclaimer, the term of this patent is extended or adjusted under 35 U.S.C. 154(b) by 238 days.

(21) Appl. No.: 14/430,486

(22) PCT Filed: Dec. 7, 2012

(86) PCT No.: PCT/US2012/068613
§ 371 (c)(1),
(2) Date: Mar. 23, 2015

(87) PCT Pub. No.: WO2014/046697
PCT Pub. Date: Mar. 27, 2014

(65) Prior Publication Data
US 2015/0246832 A1    Sep. 3, 2015

Related U.S. Application Data (60) Provisional application No. 61/704,401, filed on Sep. 21, 2012, provisional application No. 61/706,670, (Continued)

(51) Int. Cl.
*C02F 1/461* (2006.01)
*C02F 9/00* (2006.01)
(Continued)

(52) U.S. Cl.
CPC ............ *A61K 33/14* (2013.01); *A61K 31/192* (2013.01); *A61K 31/20* (2013.01); *A61K 31/216* (2013.01);
(Continued)

(58) Field of Classification Search
CPC .............. C02F 1/46104; C02F 1/46109; C02F 1/4618; C02F 2001/46185; C02F 2001/4619; C02F 2001/46195
See application file for complete search history.

(56) References Cited

U.S. PATENT DOCUMENTS

| | | |
|---|---|---|
| 4,177,116 A | 12/1979 | de Nora et al. |
| 5,234,563 A | 8/1993 | Arai |

(Continued)

FOREIGN PATENT DOCUMENTS

| | | |
|---|---|---|
| EP | 1386887 | 2/2004 |
| JP | 52-7898 | 1/1977 |

(Continued)

OTHER PUBLICATIONS

International Search Report and Written Opinion dated Jun. 10, 2013 in application No. PCT/US2012/068613, which is related to the present application.

(Continued)

*Primary Examiner* — Ibrahime A Abraham
*Assistant Examiner* — Salil Jain
(74) *Attorney, Agent, or Firm* — Knobbe Martens Olson & Bear LLP (57) ABSTRACT

Described herein are systems, apparatus, and methods for electrolyzing liquids to create beneficial compositions, such as life enhancing compositions.

14 Claims, 6 Drawing Sheets

Related U.S. Application Data filed on Sep. 27, 2012, provisional application No. 61/707,141, filed on Sep. 28, 2012.

(51) Int. Cl.

| | | |
|---|---|---|
| A61K 33/14 | (2006.01) | |
| C02F 1/467 | (2006.01) | |
| C25B 9/08 | (2006.01) | |
| A61K 31/192 | (2006.01) | |
| A61K 31/20 | (2006.01) | |
| A61K 31/216 | (2006.01) | |
| A61K 31/421 | (2006.01) | |
| A61K 31/422 | (2006.01) | |
| A61K 31/4439 | (2006.01) | |
| A61K 31/557 | (2006.01) | |
| A61K 33/00 | (2006.01) | |
| A61K 45/06 | (2006.01) | |
| C02F 1/469 | (2006.01) | |

(52) U.S. Cl.
CPC .......... *A61K 31/421* (2013.01); *A61K 31/422* (2013.01); *A61K 31/4439* (2013.01); *A61K 31/557* (2013.01); *A61K 33/00* (2013.01); *A61K 45/06* (2013.01); *C02F 1/467* (2013.01); *C02F 1/4618* (2013.01); *C02F 1/4698* (2013.01); *C02F 1/46104* (2013.01); *C25B 9/08* (2013.01); *C02F 1/46109* (2013.01); *C02F 2201/4611* (2013.01); *C02F 2201/46115* (2013.01); *C02F 2201/46155* (2013.01)

(56) References Cited

U.S. PATENT DOCUMENTS

| | | | |
|---|---|---|---|
| 5,798,028 A | 8/1998 | Tsuchikawa et al. | |
| 5,833,831 A | 11/1998 | Kitajim et al. | |
| 6,117,285 A | 9/2000 | Welch et al. | |
| 2005/0126928 A1 | 6/2005 | Hung et al. | |
| 2006/0076248 A1 | 4/2006 | Kindred | |
| 2006/0260953 A1* | 11/2006 | Hopkins | A22C 21/0061 205/701 |
| 2007/0187263 A1* | 8/2007 | Field | C02F 1/4618 205/742 |
| 2008/0292537 A1 | 11/2008 | Sano et al. | |
| 2009/0314657 A1* | 12/2009 | Field | A47L 13/26 205/770 |
| 2010/0294653 A1* | 11/2010 | Kiefer | C02F 1/4618 204/275.1 |
| 2011/0100889 A1* | 5/2011 | Saito | C02F 1/46104 210/192 |
| 2013/0048491 A1* | 2/2013 | Hung | C02F 1/46104 204/230.2 |

FOREIGN PATENT DOCUMENTS

| | | |
|---|---|---|
| JP | 54-17375 | 2/1979 |
| JP | 06-158378 | 6/1994 |
| WO | 2004-007376 | 1/2004 |

OTHER PUBLICATIONS

Extended European Search Report dated May 3, 2016 in patent application No. 12884838.9, which is related to the present application.

* cited by examiner

| Anode | | | Cathode | | | | |
|---|---|---|---|---|---|---|---|
| + | | e−↑ | e−↓ | | | − | |
| | | | | | | | 1st Generation |
| −1.23 V: $O_2$ :4H$^+$ | 4e ↑ | 2H$_2$O | 2H$^+$ | 2e ↓ | H$_2$ | :−0.00V | |
| −0.40V: $O_2$ | 4e ↑ | 4OH$^-$ | 2H$_2$O | 2e ↓ | H$_2$ 2OH$^-$ | :−0.83V | |
| −.89V: ClO$^-$ :H$_2$O | 2e ↑ | 2OH$^-$ Cl$^-$ | 2H$_2$O | 2e ↓ | 2H$^+$ H$_2$O$_2$ | :1.76V | |
| −1.36 V: Cl$_2$ | 2e ↑ | 2Cl$^-$ | Na$^+$ | 1e ↓ | Na$_{(s)}$ | :−2.71V | |
| | | | | | | | 2nd Generation |
| −1.63V :2HClO :2H$^+$ | 2e ↑ | Cl$_2$ 2H$_2$O | O$_2$ | 1e ↓ | O$_2$*$^-$ | :−0.33V | |
| −1.67V :HClO$_2$ :2H$^+$ | 2e ↑ | HClO H$_2$O | O$_2$ H$^+$ | 1e ↓ | HO$_2$* | :−0.13V | |
| −2.07V :O$_3$ :2H$^+$ | 2e ↑ | O$_2$ H2O | O$_2$ H$^+$ | 2e ↓ | H$_2$O$_2$ | :0.70V | |
| −1.18V :2ClO$_3^-$ 12H$^+$ | 10e↑ | ICl$_2$ 6H$_2$O | 2HClO 2H$^+$ | 2e ↓ | Cl$_2$ 2H$_2$O | :1.63V | |
| | | | | | | | 3rd Generation+ |
| −1.19V :ClO$_2$ :H$^+$ | 1e ↑ | HClO$_2$ H$_2$O | HO$_2$* | 1e ↓ | H$_2$O$_2$ | :1.51V | |
| −1.18V :ClO$_3^-$ :2H$^+$ | 1e ↑ | ClO$_2$ H$_2$O | H$_2$ | 2e ↓ | 2H$^-$ | :−2.25V | |

*FIG. 6*

CELL FOR ELECTROLYZING A LIQUID

CROSS REFERENCE TO RELATED APPLICATIONS

This application claims the benefit of U.S. provisional patent application Nos. 61/704,401 filed Sep. 21, 2012, 61/706,670 filed Sep. 27, 2012, and 61/707,141 filed Sep. 28, 2012, the disclosures each of which are incorporated herein by reference in their entirety.

FIELD

Described herein are cells for electrolyzing one or more liquids.

SUMMARY

Described generally herein are electrolyzing systems including a first chamber including at least one cathode configured to electrolyze a first salinated water stream and create a high pH product. Also included is a second chamber including at least one anode configured to electrolyze a second salinated water stream and create a low pH product. A membrane can exist between the first chamber and the second chamber configured to allow ions through and prevent water from passing.

Methods of forming electrolyzed solutions are also described comprising: supplying a first salinated water stream to a first chamber including at least one cathode configured to electrolyze the first salinated water stream and create a high pH product. Also, the methods can include supplying a second salinated water stream to a second chamber including at least one anode configured to electrolyze the second salinated water stream and create a low pH product. A voltage can be applied across the cathode and anode to electrolyze the first salinated water stream and the second salinated water stream while providing a membrane separating the first chamber and the second chamber. The membrane can be configured to prevent water from passing between the first chamber and the second chamber and allows ions through.

The second chamber can include an inlet in the anode and the second salinated water stream can reside within at most 5 inches of a surface of the anode for at least 1 second to electrolyze the second salinated water stream.

Also described herein are continuous flow electrolyzing systems for contemporaneously producing multiple product lines comprising: a first chamber including at least one cathode configured to electrolyze a first salinated water stream; a second chamber including at least one anode configured to electrolyze a second salinated water stream; and a power source. In some embodiments, the second chamber includes at least two sub-chambers and at least one anode in each sub-chamber. The power source can apply a voltage between at least one cathode and at least one anode in each sub-chamber to electrolyze the first salinated water stream and the second salinated water stream. Each of the at least two sub-chambers can be at least partly contiguous with the first chamber such that at least one ion of the salinated water stream from the first chamber flows into each of the sub-chambers. In one embodiment, the at least one cathode is no more than about 3 inches from at least one anode in each of the sub-chambers. The flow of water through such systems can be continuous or can be sporadic in nature.

DETAILED DESCRIPTION

Described herein are systems, apparatus and methods which can be used to form life enhancing compositions or beverages. The methods generally include electrolyzing a salinated solution using an apparatus or system as described herein to produce a life enhancing beverage. The life enhancing beverages generally include at least one reactive species such as a reactive oxygen species (ROS). In other embodiments, the beverages can include chlorine, $OCl^-$ and/or $O^{-2}$. In some embodiments, the life enhancing beverages can have a saline concentration of about 0.15% w/v.

The life enhancing beverages can induce, supply, produce, contribute to, supplement, improve, or augment a positive human feature. Positive human features can include drug acceptance, healing, increasing immunity, increasing serum levels of beneficial metabolites such as but not limited to ascorbic acid, and the like.

Superoxide free radicals ($OO^{*-}$ and $OOH^*$) and hydroxyl free radicals ($OH^*$) can have a short half-life in aqueous solutions ($t(\frac{1}{2}) < 2$ ms). In one embodiment, apparatus, systems, and methods are described which can produce these biologically reactive components in aqueous solutions with half lives of, for example, several years, sufficient for long-term storage. Such stable complexes and compositions also include reductive components, such that the combined composition can have a neutral pH. Also, the produced compositions may not result in any toxicity in vitro and/or in vivo.

The electro-catalytic process that forms such biologically reactive components can rely heavily on the purity and molecular homogeneity of the reactants as they make contact with the local reactive surfaces of electrodes. Preparation of an ultra pure salinated solution can be a critical step in the process for use in the described apparatus. The salinated solution generally should be free from contaminants, both organic and inorganic, and homogeneous down to the molecular level. In particular, metal ions can interfere with the electro-catalytic surface reactions, and thus contamination of the water or saline by metals should be avoided.

The systems, apparatus, and methods described herein can more efficiently produce life enhancing beverages and compositions than previous systems. For example, using the herein described systems, apparatus and methods, one or more of the following can be achieved: higher throughput, lower voltage required to electrolyze, higher flow rates, less requirement to chill solutions, less time required at each electrode, more efficient electrolysis, simultaneous production of multiple product lines, and the like.

A salinated solution for use in the described apparatus and systems can be prepared as follows. Water can be supplied from a variety of sources, including but not limited to municipal water, filtered water, nanopure water, or the like.

Municipal water, for example, can be highly variable depending on the water source (e.g. stream or river versus surface or underground reservoir water), the method of sterilizing the water prior to distribution (e.g., UV light), chemicals used to treat the water, and the like. Regardless of the source of water, optionally, reverse osmosis can be used to reproducibly clean the water.

The reverse osmosis process can vary, but can provide purified water having a total dissolved solids content of less than about 10 ppm, about 9 ppm, about 8 ppm, about 7 ppm, about 6 ppm, about 5 ppm, about 4 ppm, about 3 ppm, about 2 ppm, about 1 ppm, 0.5 ppm, less than about 10 ppm, less than about 9 ppm, less than about 8 ppm, less than about 7 ppm, less than about 6 ppm, less than about 5 ppm, less than about 4 ppm, less than about 3 ppm, less than about 2 ppm, or less than about 1 ppm.

The reverse osmosis process can be performed at a temperature of about 5° C., about 10° C., about 15° C., about 20° C., about 25° C., about 30° C., or about 35° C., from about 5° C. to about 35° C., from about 10° C. to about 25° C., from about 5° C. to about 25° C., from about 10° C. to about 35° C., from about 20° C. to about 30° C., less than about 35° C., less than about 30° C., less than about 25° C., less than about 20° C., greater than about 5° C., greater than about 10° C., greater than about 15° C., or greater than about 20° C.

The reverse osmosis step can be repeated as needed to achieve a particular total dissolved solids level. Whether the optional reverse osmosis step is utilized, an optional distillation step can be performed to clean or further clean the water.

The distillation process can vary, but can provide purified water having a total dissolved solids content of less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, less than about 1 ppm, less than about 0.9 ppm, less than about 0.8 ppm, less than about 0.7 ppm, less than about 0.6 ppm, less than about 0.5 ppm, less than about 0.4 ppm, less than about 0.3 ppm, less than about 0.2 ppm, or less than about 0.1 ppm.

The distillation process can be performed at a temperature of about 5° C., about 10° C., about 15° C., about 20° C., about 25° C., about 30° C., or about 35° C., from about 5° C. to about 35° C., from about 10° C. to about 25° C., from about 5° C. to about 25° C., from about 10° C. to about 35° C., from about 20° C. to about 30° C., less than about 35° C., less than about 30° C., less than about 25° C., less than about 20° C., greater than about 5° C., greater than about 10° C., greater than about 15° C., or greater than about 20° C. In one embodiment, the distillation can be run at about room temperature.

The distillation step can be repeated as needed to achieve a particular a total dissolved solids level. After water has been subjected to reverse osmosis, distillation, both or neither, the level of total dissolved solids in the water can be less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, less than about 1 ppm, less than about 0.9 ppm, less than about 0.8 ppm, less than about 0.7 ppm, less than about 0.6 ppm, less than about 0.5 ppm, less than about 0.4 ppm, less than about 0.3 ppm, less than about 0.2 ppm, or less than about 0.1 ppm. The amount of total dissolved solids in the water can be an important aspect in the final product as some solids can lead to contaminants during or after electrolyzing.

Purified water can be used directly with the systems and methods described herein. For example, in one embodiment, if purified water is used that has a total dissolved solids concentration of less than about 0.5 ppm, neither reverse osmosis nor distillation needs to be used. In other embodiments, if semi-purified water is used, only one of the processes may be required.

In one embodiment, contaminants can be removed from a commercial source of water by the following procedure: water flows through an activated carbon filter to remove the aromatic and volatile contaminants and then undergoes Reverse Osmosis (RO) filtration to remove dissolved solids and most organic and inorganic contaminants. The resulting filtered RO water can contain less than about 8 ppm of dissolved solids. Most of the remaining contaminants can be removed through a distillation process, resulting in dissolved solid measurements less than 1 ppm. In addition to removing contaminants, distillation may also serve to condition the water with the correct structure and Oxidation Reduction Potential (ORP) to facilitate the oxidative and reductive reaction potentials on the platinum electrodes in the subsequent electro-catalytic process.

After water has been subjected to reverse osmosis, distillation, both or neither, a salt is added to the water in a salting step. The salt can be unrefined, refined, caked, de-caked, or the like. In one embodiment, the salt is sodium chloride (NaCl). In other embodiments, the salt can be a chlorine based salt such as, but not limited to, LiCl, HCl, $CuCl_2$, $CuSO_4$, KCl, MgCl, sulfates and phosphates. In other embodiments, the salt can be any ionic salt such as, but not limited to, fluoride, sulfate, ammonium, calcium, iron, magnesium, potassium, pyridinium, Quaternary ammonium, sodium, acetate, carbonate, citrate, cyanide, nitrate, nitrite, phosphate salts, combinations thereof, or analogues thereof.

In some embodiments, the salt can include an additive. Salt additives can include, but are not limited to potassium iodide, sodium iodide, sodium iodate, dextrose, sodium fluoride, sodium ferrocyanide, tricalcium phosphate, calcium carbonate, magnesium carbonate, fatty acids, magnesium oxide, silicone dioxide, calcium silicate, sodium aluminosilicate, calcium aluminosilicate, ferrous fumarate, iron, or folic acid. Any of these additives can be added at this point or at any point during the described process. For example, the above additives can be added just prior to bottling.

Salt can be added to water in the form of a brine solution. Brine can be formed at a salt ratio of about 500 g NaCl/gal water, about 505 g NaCl/gal water, about 510 g NaCl/gal water, about 515 g NaCl/gal water, about 520 g NaCl/gal water, about 525 g NaCl/gal water, about 530 g NaCl/gal water, about 535 g NaCl/gal water, about 536 g NaCl/gal water, about 537 g NaCl/gal water, about 538 g NaCl/gal water, about 539 g NaCl/gal water, about 540 g NaCl/gal water, about 545 g NaCl/gal water, about 550 g NaCl/gal water, about 555 g NaCl/gal water, about 560 g NaCl/gal water, about 565 g NaCl/gal water, about 570 g NaCl/gal water, about 575 g NaCl/gal water, about 580 g NaCl/gal water, between about 500 g NaCl/gal water and about 580 g NaCl/gal water, between about 520 g NaCl/gal water and about 560 g NaCl/gal water, or between about 535 g NaCl/gal water and about 540 g NaCl/gal water. In one embodiment, the ratio can be about 537.5 g NaCl/gal water. Equivalent amounts of other salts can be calculated based on their stoichiometric rations.

Brine can be formed by adding NaCl or another salt to purified water in a tank. The brine solution can then be thoroughly mixed for about 30 min, about 1 hr, about 6 hr, about 12 hr, about 1 day, about 2 days, about 3 days, about 4 days, about 5 days, about 6 days, about 7 days, about 8 days, about 9 days, about 10 days, or longer.

To mix the brine solution, a physical mixing apparatus can be used or a circulation or recirculation can be used. A tank of any appropriate size to form a brine solution can be used. In one embodiment a brine solution can be circulated or re-circulated at a rate of about 0.5 gal/hr, about 1 gal/hr, about 5 gal/hr, about 10 gal/hr, about 15 gal/hr, about 20 gal/hr, about 30 gal/hr, about 40 gal/hr, about 50 gal/hr, about 60 gal/hr, about 70 gal/hr, about 80 gal/hr, about 90 gal/hr, about 100 gal/hr, about 200 gal/hr, about 300 gal/hr, about 400 gal/hr, about 500 gal/hr, about 600 gal/hr, about 700 gal/hr, about 800 gal/hr, about 900 gal/hr, about 1,000 gal/hr, about 1,100 gal/hr, about 1,200 gal/hr, about 1,300 gal/hr, about 1,400 gal/hr, about 1,500 gal/hr, about 1,600 gal/hr, about 1,700 gal/hr, about 1,800 gal/hr, about 1,900 gal/hr, about 2,000 gal/hr, about 2,100 gal/hr, about 2,200 gal/hr, about 2,300 gal/hr, about 2,400 gal/hr, about 2,500 gal/hr, or higher. The amount of mixing time or type of mixing used can vary. However, in some embodiments, at the end of mixing, all the salt can be dissociated.

In one embodiment, pure pharmaceutical grade sodium chloride is dissolved in the prepared distilled water to form a 15 w/w % sub-saturated brine solution and continuously re-circulated and filtered until the salt has completely dissolved and all particles >0.1 microns are removed. This step can take several days. The filtered, dissolved brine solution can then be injected into tanks of distilled water in about a 1:352 ratio (salt:water) in order to form a 0.3% saline solution. In one embodiment, a ratio 10.75 g of salt per 1 gallon of water can be used to form the beverage. In another embodiment, 10.75 g of salt per 3,787.5 g of water can be used to form the beverage. This solution then can be allowed to re-circulate and diffuse until homogeneity at the molecular scale has been achieved. The diffusion coefficient of this brine in distilled water is about $1.5 \times 10^{-9}$ m$^2$/s at 25° C. The Einstein diffusion time ($t=<x>2/2D$) can then be used to determine the time it will take for the sodium chloride ions to diffuse completely in the saline solution. About 5 min may be required for molecules to completely diffuse 1 mm from concentration centers, and 500 min are required for the molecules to diffuse 1 cm based on the above approximation.

Mechanical mixing through recirculation can be required to speed diffusion. Also, the system can remain closed to prevent atmospheric contamination.

In one embodiment, the homogenous salinated solution is chilled to about 4.8±0.5° C. This temperature may be critical because higher temperatures can increase ROS content and lower temperatures can increase hypochlorite (RS) and possibly free chlorine content during processing. Correct balance can require precisely controlled temperature at the electro-catalytic surfaces. Careful temperature regulation during the entire electro-catalytic process is required as thermal energy generated from the electrolysis process itself may cause heating. In one embodiment, process temperatures at the electrodes can be constantly cooled and maintained at about 4.8° C. throughout electrolysis.

Brine can then be added to the previously treated water or to fresh untreated water to achieve a NaCl concentration of about 1 g NaCl/gal water, about 2 g NaCl/gal water, about 3 g NaCl/gal water, about 4 g NaCl/gal water, about 5 g NaCl/gal water, about 6 g NaCl/gal water, about 7 g NaCl/gal water, about 8 g NaCl/gal water, about 9 g NaCl/gal water, about 10 g NaCl/gal water, about 10.25 g NaCl/gal water, about 10.50 g NaCl/gal water, about 10.75 g NaCl/gal water, about 11 g NaCl/gal water, about 12 g NaCl/gal water, about 13 g NaCl/gal water, about 14 g NaCl/gal water, about 15 g NaCl/gal water, about 16 g NaCl/gal water, about 17 g NaCl/gal water, about 18 g NaCl/gal water, about 19 g NaCl/gal water, about 20 g NaCl/gal water, about 21 g NaCl/gal water, about 22 g NaCl/gal water, about 23 g NaCl/gal water, about 24 g NaCl/gal water, about 25 g NaCl/gal water, between about 1 g NaCl/gal water and about 25 g NaCl/gal water, between about 8 g NaCl/gal water and about 12 g NaCl/gal water, or between about 4 g NaCl/gal water and about 16 g NaCl/gal water.

Once brine is added to water in an appropriate amount, the solution can be thoroughly mixed for about 30 min, about 1 hr, about 6 hr, about 12 hr, about 24 hr, about 36 hr, about 48 hr, about 60 hr, about 72 hr, about 84 hr, about 96 hr, about 108 hr, about 120 hr, about 132 hr, or longer, no less than about 12 hr, no less than about 24 hr, no less than about 36 hr, no less than about 48 hr, no less than about 60 hr, no less than about 72 hr, no less than about 84 hr, no less than about 96 hr, no less than about 108 hr, no less than about 120 hr, or no less than about 132 hr.

The temperature of the liquid during mixing can be at room temperature or controlled at a temperature of about 20° C., about 25° C. about 30° C. about 35° C. about 40° C. about 45° C. about 50° C. about 55° C., about 60° C., between about 20° C. and about 40° C., between about 30° C. and about 40° C., between about 20° C. and about 30° C., between about 25° C. and about 30° C., or between about 30° C. and about 35° C.

To mix the solution, a physical mixing apparatus can be used or a circulation or recirculation can be used. In some embodiments, the mixing time can be sufficient to allow complete dissociation of the NaCl.

The salt solution can then be chilled in a chilling step prior to injection or input and subsequent electrolysis in the below described apparatus. The temperature of the chilled solution can be about 0° C., about 1° C. about 2° C. about 3° C. about 4° C. about 5° C. about 6° C. about 7° C., about 8° C., about 9° C., about 10° C., about 11° C., about 12° C., between about 0° C. and about 10° C., between about 0° C. and about 5° C., between about 5° C. and about 10° C., between about 0° C. and about 7° C., or between about 2° C. and about 5° C. In one embodiment, the chilled solution can have a temperature of between about 4.5° C. and about 5.8° C.

For large amounts of pre-injection solution, various chilling and cooling methods can be employed. For example cryogenic cooling using liquid nitrogen cooling lines can be used. Likewise, the solution can be run through propylene glycol heat exchangers to achieve the desired temperature. The chilling process can take about 5 min, about 10 min, about 20 min, about 30 min, about 1 hr, about 2 hr, about 3 hr, about 4 hr, about 5 hr, about 6 hr, about 7 hr, about 8 hr, about 9 hr, about 10 hr, about 12 hr, about 14 hr, about 16 hr, about 18 hr, about 20 hr, about 22 hr, about 24 hr, between about 30 min and about 24 hr, between about 1 hr and about 12 hr, at least about 30 min, at least about 6 hr, at most about 24 hr, or any range created using any of these values to get the solution from room temperature to a desired chilled temperature. The chilling time can vary depending on the amount of liquid, the starting temperature and the desired chilled temperature. A skilled artisan can calculate the time required to chill a solution as described.

Then, chilled or un-chilled room temperature brine solution as created above can be added to an electrolysis device. A device or cell for electrolyzing salinated water is illustrated in FIGS. 1-5. Cell 100 can generally be formed in three separable parts, a top plate 102, a circumferential body ring 104, and a bottom plate 106. One or more gaskets can be used to seal the parts together and other o-rings or seals can be used to make cell 100 water tight. For example, first gasket 108 can fill any gap between top plate 102 and circumferential body ring 104, and second gasket 110 can fill any gap between bottom plate 106 and circumferential body ring 104. One or more bolts 112 can be used to hold the three pieces together including any gaskets. In some embodiments, the entire cell body can be fabricated from a single piece of material.

As illustrated in FIGS. 1-5, cell 100 can have a generally round and/or cylindrical shape. However, a cell can have any shape that can allow for formation of a desired electrolyzed product. For example, a cell can have a generally rectangular shape, a triangular shape, an elliptical shape, a clovered shape, a square shape, a linear shape, a combination thereof or the like.

In order to electrolyze liquids, cell 100 includes at least one cathode 114 and at least one anode 116. Depending on the configuration of a cell, any number of anodes or cathodes can be used that allows for a liquid to be sufficiently electrolyzed. In one embodiment, cell 100 can include 12 anodes and 12 cathodes. In other embodiments, a cell can include two, three, four, five, six, seven, eight, nine, ten, eleven, twelve, 13, 14, 15, 16, 17, 18, 19, 20, 25, 30, 35, 40, 45, 50, 60, 70, 80, 90, 100, 125, 150, 175, 200, or more anodes, and two, three, four, five, six, seven, eight, nine, ten, eleven, twelve, 13, 14, 15, 16, 17, 18, 19, 20, 25, 30, 35, 40, 45, 50, 60, 70, 80, 90, 100, 125, 150, 175, 200, or more cathodes.

Anodes 116 and cathodes 114 can be or include a conductive metal. Metals can include, but are not limited to copper, aluminum, titanium, tantalum, niobium, ruthenium, rhodium, palladium, platinum, silver, osmium, gold, iron, a combination thereof or an alloy such as steel or brass. The electrode can be coated or plated with a different metal such as, but not limited to aluminum, gold, platinum or silver, or any other metal described above.

In one embodiment, each electrode is formed of titanium and plated with platinum. The platinum surfaces on such anodes and cathodes can be optimal to catalyze the required reactions. Rough, double layered platinum plating can assure that local "reaction centers" (sharply pointed extrusions) are active and that the reactants not make contact with the underlying electrode titanium substrate. Double plated platinum can minimize the risk of micropores in the platinum surface going through to the titanium. During electrolysis, oxygen and hydrogen bubbles themselves can form on the platinum surfaces during electrolysis and reduce the reactive surface area. Sharp, uneven surfaces can tend to minimize bubble adhesion and create stronger local electric fields, increasing efficiency. In one embodiment, anodes 116 and cathodes 114 can be rough platinum-plated mesh.

In another embodiment, anodes 116 and cathodes 114 can be have no more than about 0.5 in, about 1 in, about 1.5 in, about 2 in, about 2.5 in, about 3 in, about 3.5 in, about 4 in, about 4.5 in, about 5 in, about 5.5 in, about 6 in, about 6.5 in, about 7 in, about 7.5 in, about 8 in, about 9 in, about 10 in, about 12 in, about 14 in, or about 20 in of separation between them. The height of the electrodes also can be important, as tall electrodes can promote inconsistent flow of fluids from bottom to top, as well as dissolved-oxygen gradients from bubbles generated. These factors can disrupt consistent homogeneity and uniform anode to cathode flow when comparing the bottom and top of the electrodes. Electrodes can have a diameter of about 1/64 in, about 1/32 in, about 1/16 in, about 1/8 in, about 1/4 in, about 1/2 in, about ¾ in, or about 1 in, with heights not exceeding about 1 in, about 2 in, about 3 in, about 4 in, about 5 in, about 6 in, about 7 in, about 8 in, about 10 in, about 12 in, or about 14 in.

In one embodiment, tilting the electrodes slightly may help offset the uneven-dissolved-oxygen effect. Inconsistent spacing between the electrodes can also be disruptive. Electrical current can be significantly higher between the closer-spaced surfaces of the electrodes, causing over-processing in these regions and robbing electrical current and proper reactions from surfaces that are farther apart. Inconsistencies in electrode spacing can also cause inconsistent and unpredictable results.

Anodes 116 and cathodes 114 can be generally cylindrical in shape, but can also assume other shapes that can allow proper electrolysis of the target fluid. Other shapes can include, but are not limited to shapes having an oval cross-section, square cross-section, rectangular cross-section, triangular cross-section, star-shaped cross-section, torx shaped cross-section, or the like.

Anodes 116 and cathodes 114 can be held in cell 100 using any means that can sufficiently hold the electrode in place without allowing water the substantially leak from the cell. For example, in one embodiment, anode 116 and cathode 114 can be screwed into a pre-threaded hole within cell 100 to hole it in place. In such an embodiment, on the opposite side on the electrode can be a friction fit using an o-ring that engages a securing plate fit to top plate 102 or bottom plate 106 with a gasket. Such a configuration allows for simple and efficient changing of electrodes. For example, to remove and electrode, it can be unplugged, unscrewed, and simply pulled of cell 100. To install a new electrode, the opposite can be performed. In one embodiment, when liquid is inputted through anode 116, the threaded side of the electrode can also act as the liquid input port.

The amperage run through each electrode can be about 0.01 amps, about 0.05 amps, about 0.05 amps, about 1 amp, about 2 amps, about 3 amps, about 4 amps, about 5 amps, about 6 amps, about 7 amps, about 8 amps, about 9 amps, about 10 amps, about 11 amps, about 12 amps, about 13 amps, about 14 amps, or about 15 amps, between about 0.01 amps and about 15 amps, between about 0.5 amps and about 14 amps, at least about 0.01 amps, at least about 0.05 amps, at least about 0.5 amps, or any range created using any of these values.

In one embodiment, each cathode 114 can be driven by the same voltage, each cathode 114 can be driven by a different voltage, or a combination thereof. The same can be true for the anodes. In one embodiment, each anode 116 can be driven by the same voltage, each anode 116 can be driven by a different voltage, or a combination thereof. Appropriate voltage can be about 1V, about 5V, about 10V, about 15V, about 20V, about 25V, about 30V, about 35 V, about 40V, about 50V, at least about 5V, at least about 25V, between about 1V and about 50V, between about 20V and about 40 V, at most about 40V, at most about 30V, at most about 25V, or at most about 20V.

The solution can be chilled during the electrochemical process. The temperature during this process can be about 0° C., about 1° C. about 2° C. about 3° C. about 4° C. about 5° C. about 6° C. about 7° C., about 8° C., about 9° C., about 10° C., about 11° C., about 12° C., between about 0° C. and about 10° C., between about 0° C. and about 5° C., between about 5° C. and about 10° C., between about 0° C. and about 7° C., or between about 2° C. and about 5° C. In one embodiment, the chilled solution can have a temperature of between about 4.5° C. and about 5.8° C.

Figure 1:
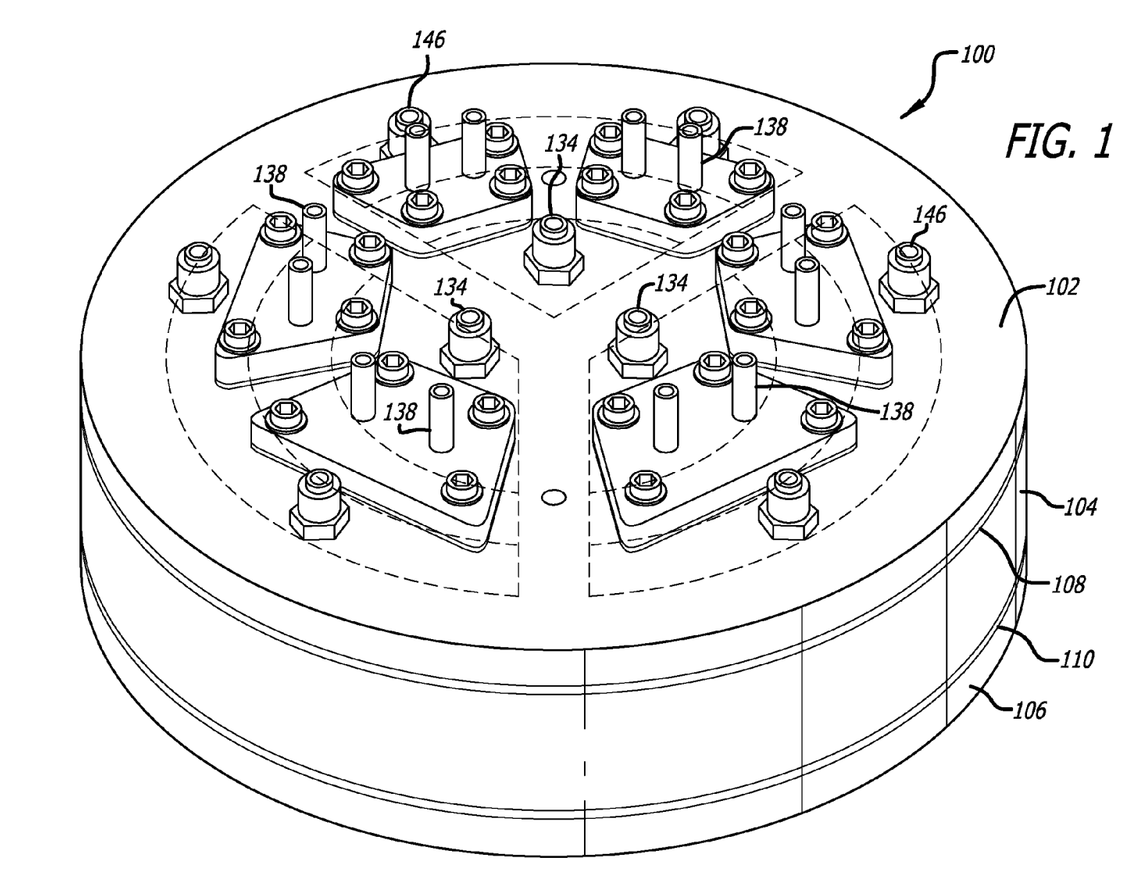
FIG. 1 illustrates a top perspective view of a cell as described herein.
Figure 2:
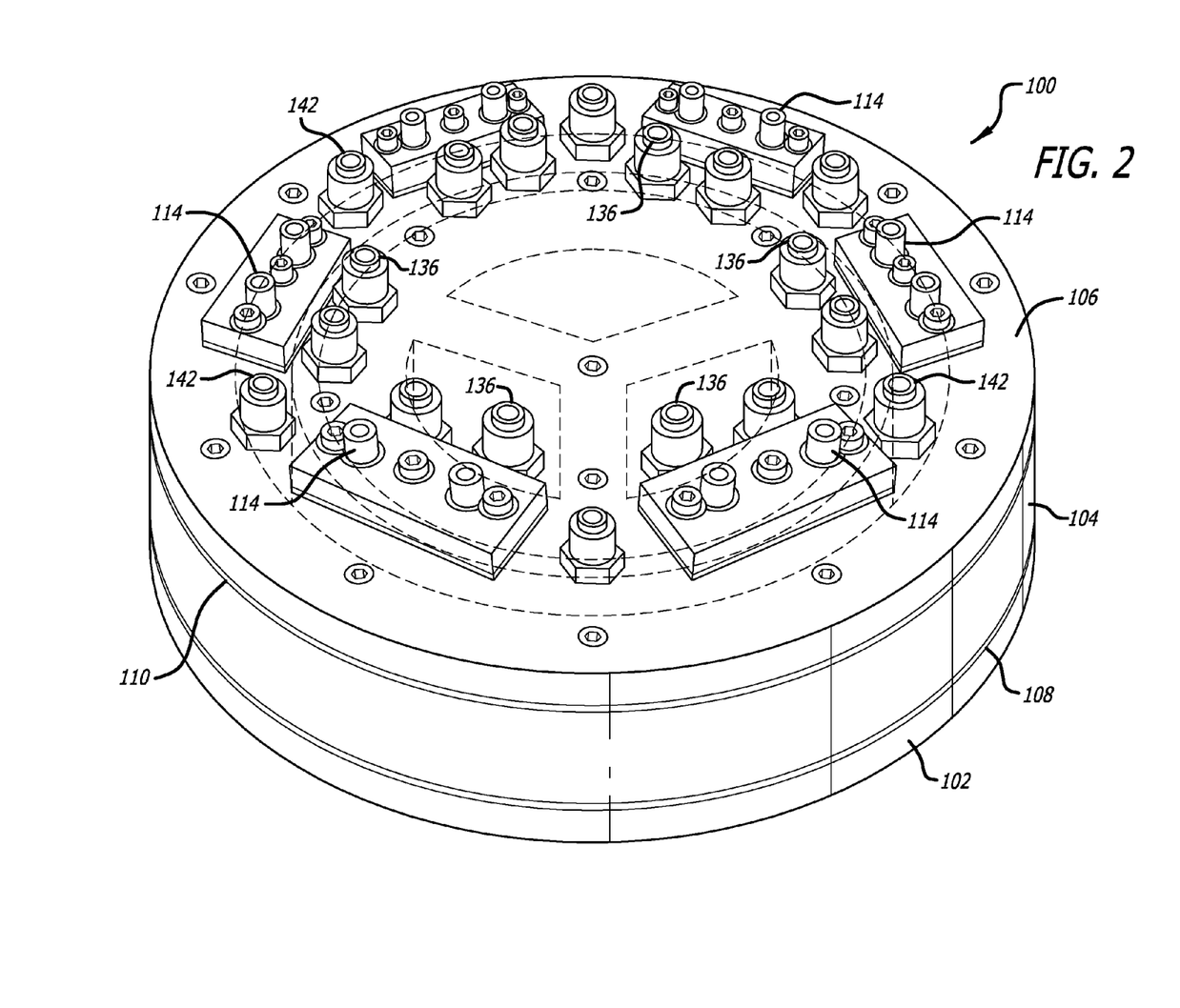
FIG. 2 illustrates a bottom perspective view of a cell as described herein.
Figure 3:
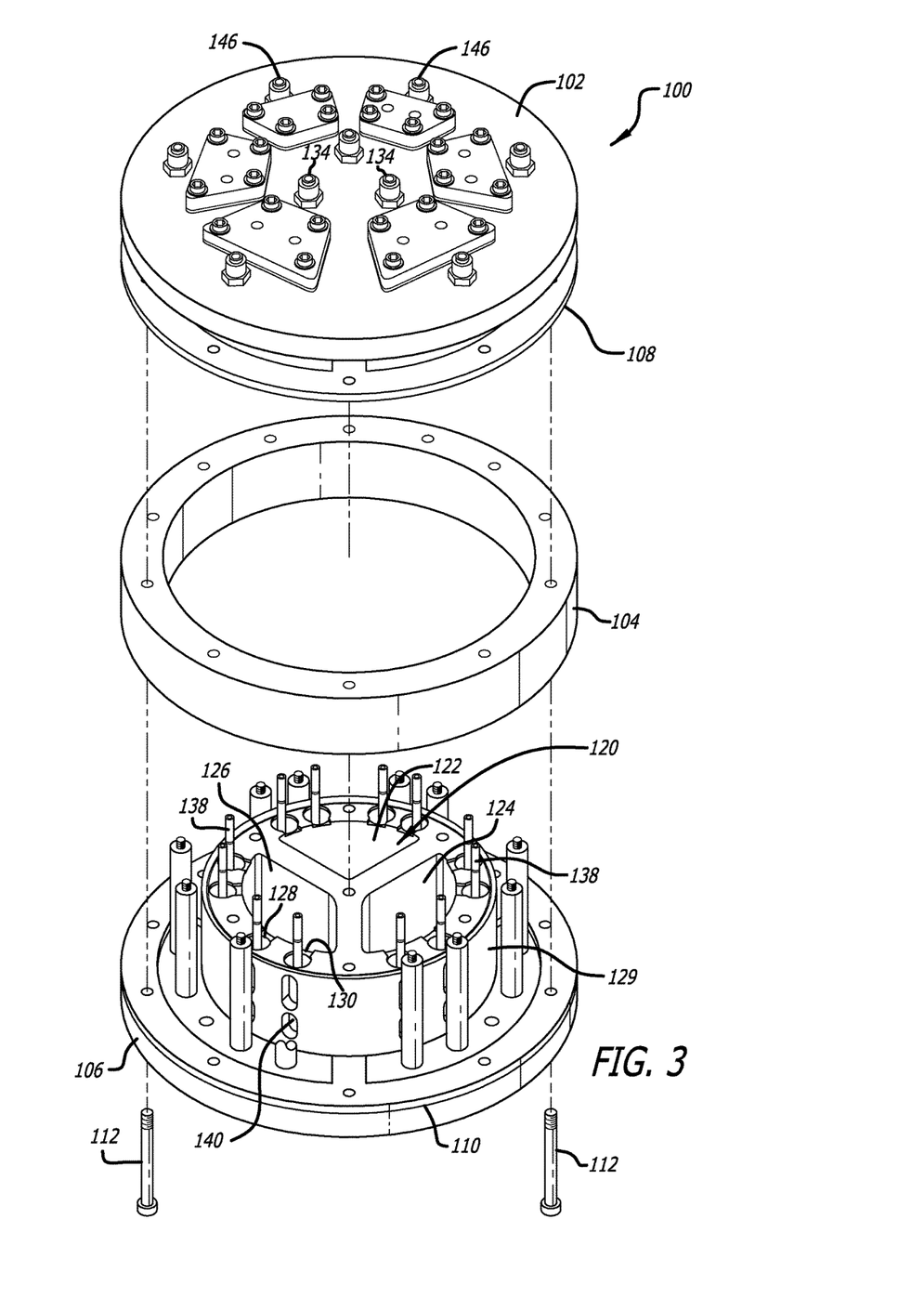
FIG. 3 illustrates an exploded view of a cell as described herein.
Figure 4:
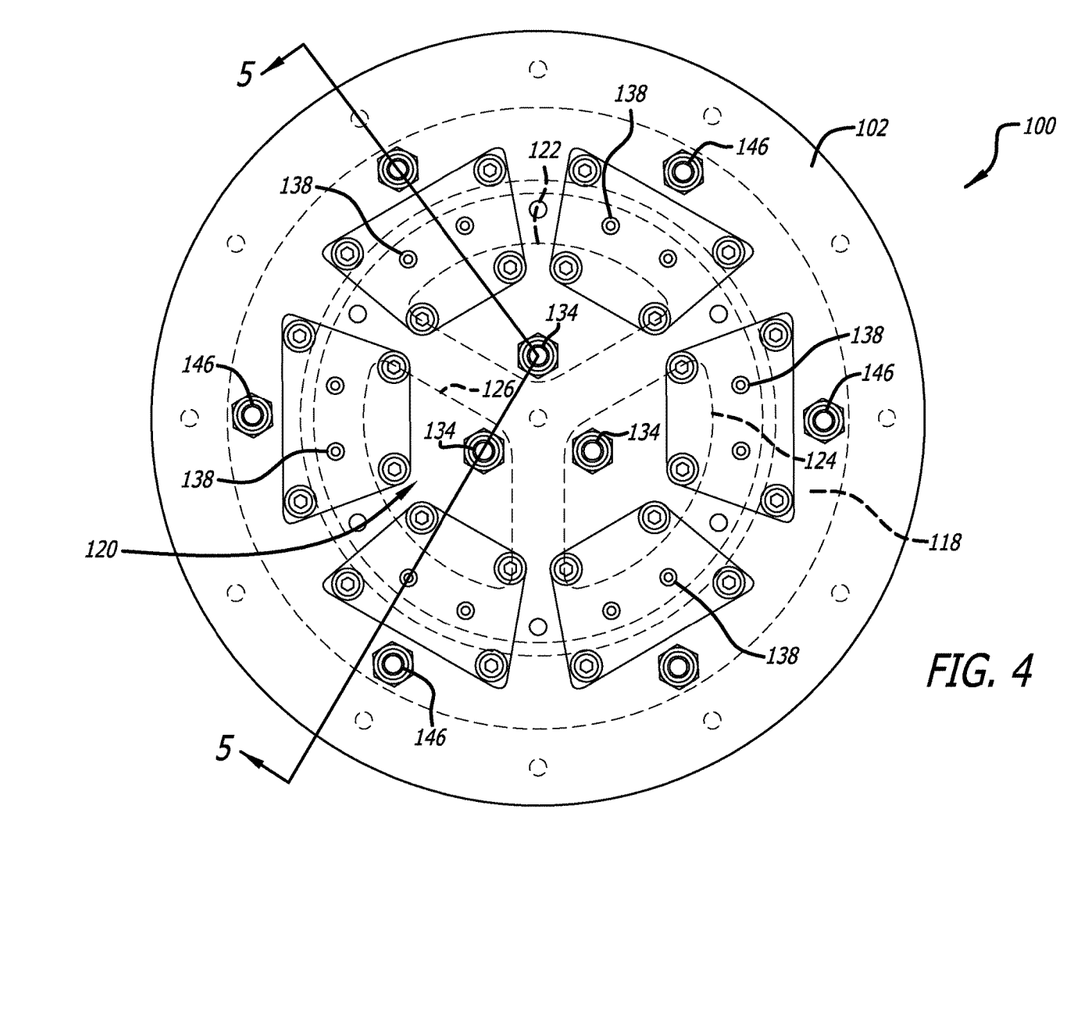
FIG. 4 illustrates a top view of a cell as described herein.

Cell 100 can further include two or more separate chambers for electrolyzing a liquid. For example, cell 100 can include a first chamber 118 housing one or more cathodes 114, and a second chamber 120 housing one or more anodes 116. Both first chamber 118 and second chamber 120 can be divided into two, three, four, five, six, seven, eight, nine, ten, eleven, twelve or more sub-chambers or can remain as one large chamber. As illustrated in FIG. 3, second chamber 120 can be equally divided into a first sub-chamber 122, a second sub-chamber 124, and a third sub-chamber 126.

First chamber 118 can be formed between the inner surface of top plate 102, the inner surface of bottom plate 106, the inner surface of circumferential body ring 104, and second chamber outer wall 129.

Figure 5:
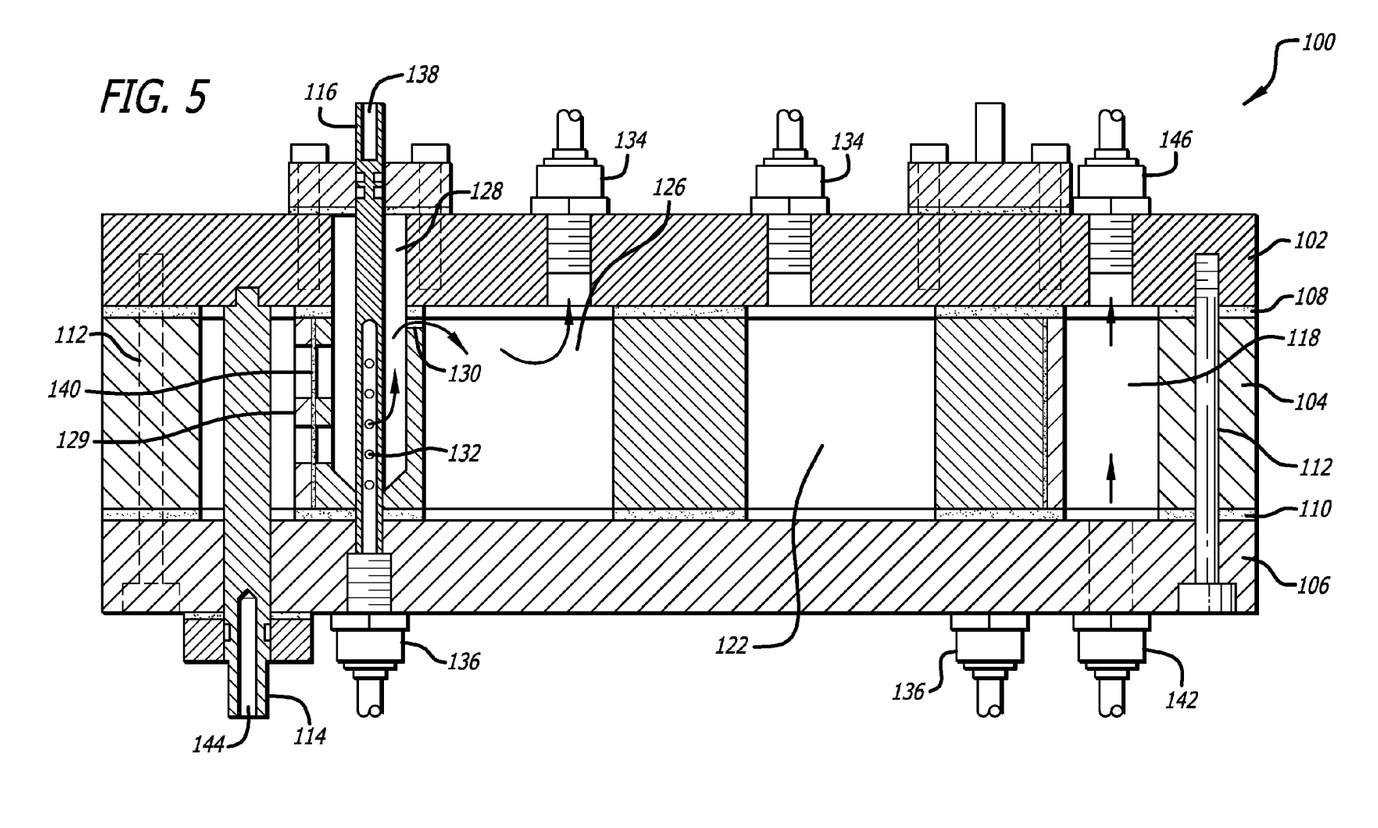
FIG. 5 is a cross-section of the cell in FIG. 4.

Second chamber 120 can include multiple sub-chambers such as a first sub-chamber 122, a second sub-chamber 124, and a third sub-chamber 126, but can also include volume surrounding one or more anodes 116. For example, as illustrated in FIGS. 3 and 5, anode 116 can be surrounded by an electrolytic volume 128. Electrolytic volume 128 can empty into second chamber 120, be considered part of second chamber 120, and/or be in fluid connection with second chamber 120. In one embodiment, electrolytic volume 128 can be connected to second chamber 120 by overflow port 130.

As overflow port 130 resides at the uppermost portion of second chamber 120, gravity will keep liquids in electrolytic volume as long as possible. In one embodiment, liquid can enter second chamber 120 through anode 116. One or more entry holes 132 can be located on anode 116. The configuration of the one or more holes 132 can dictate the flow of liquid in electrolytic volume 128. For example, holes 132 can be configured to create a vortex within electrolytic volume 128.

Again, because of gravity, liquids can be retained within electrolytic volume 128 before spilling over overflow port 130 for a period of time sufficient to electrolyze the liquid. For example, liquids can be retained for about 0.1 seconds, about 0.5 seconds, about 0.7 seconds, about 0.8 seconds, about 0.8 seconds, about 0.9 seconds, about 1 second, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 35 seconds, about 40 seconds, about 45 seconds, about 50 seconds, about 60 seconds, at least about 0.1 seconds, at least about 1 second, at least about 4 seconds, at least about 5 seconds, at least about 6 seconds, at least about 7 seconds, at least about 8 seconds, at least about 9 seconds, at least about 10 seconds, at least about 15 seconds, at least about 20 seconds, at least about 25 seconds, at least about 30 seconds, between about 0.1 seconds and about 10 seconds, between about 1 second and about 30 seconds, between about 0.1 seconds and about 5 seconds, between about 5 second and about 30 seconds, or between about 1 second and about 60 seconds.

Further, since electrolytic volume 128 has a fixed volume, liquids can be kept within a fixed distance from the anode surface for a time as described above. For example, liquids can be held within about 1/64 in, about 1/32 in, about 1/16 in, about 1/8 in, about 1/4 in, about 1/2 in, about % in, about 1 in, about 2 in, about 3 in, about 4 in, about 5 in, about 6 in, at least about 1/64 in, at most about 1/32 in, at most about 1/16 in, at most about 1/8 in, at most about 1/4 in, at most about 1/2 in, at most about % in, at most about 1 in, at most about 2 in, at most about 3 in, at most about 4 in, at most about 5 in, at most about 6 in, between about 1/64 in and about 6 in, between about 1/2 in and about 2 in, or between about 1 in and about 2 in of the anode surface.

A build-up of excessive reactive species at one or more of the electrodes can cause over-processing and build-up of undesirable reaction products in the neighborhood of the electrodes. As such, the present apparatus provide a constant homogeneous flow of reactants past at least one set of electrodes.

Electrolyzed liquid can be removed from second chamber 120 from one or more output ports 134. Output ports 134 can be located or emanate through top plate 102. Second chamber 120 can include any number of output ports 134 that allow for electrolyzed liquid to be removed as needed by the cell. For example, second chamber 120 can include two, three, four, five, six, seven, eight, nine, ten, eleven, twelve, 13, 14, 15, 16, 17, 18, 19, 20, or more output ports 134. In one embodiment, second chamber 120 can include three output ports 134. In another embodiment, second chamber 120 can include first sub-chamber 122, second sub-chamber 124, and third sub-chamber 126 each including a single output port 134.

Entry holes 132 on anode 116 can be fed from a liquid source. Input 136 can be located at the top or bottom end of anode 116. In one embodiment, input 136 can be located at the bottom of anode 116 and can directly feed entry holes 132.

At the opposite end of anode 116 from input 136 can be located electrolytic anode connection point 138. Electrolytic anode connection point 138 can be configured to hook up to an appropriately charged power source.

Across from anode 116 is cathode 114. Between anode 116 and cathode 114 can be membrane 140. Membrane 140 can be selective. Membrane 140 can be any type of selectively permeable membrane or ion exchange membrane. Ion exchange membranes can include cation exchange membranes, an anion exchange membranes, bipolar membranes, and charge mosaic membranes. Exemplary membranes can include hydroxyl ion exchange membranes. Selectively permeable membrane may only allow some ions (e.g., anion or cations) to flow through. Such selectively permeable membranes can provide a separation of the anions and cations.

In one embodiment, membrane 140 is a selectively permeable membrane or ion exchange membrane allowing ions through, but not water. Membrane 140 can be selected for a particular electrolysis scheme.

Membrane 140 can provide the entire barrier between first chamber 118 and second chamber 120. Or, in one embodiment, any number of smaller membranes can be used between pairs of electrodes. For example, one, two, three, four, five, six, seven, eight, nine, ten, eleven, twelve, 13, 14, 15, 16, 17, 18, 19, or 20 membranes can be used. In some embodiments, two or more different membranes can be used between each set of electrodes. In other embodiments, different membranes can be used between first chamber 118 and each sub-chamber in order to allow different components into different sub-chambers.

In some embodiments, no membrane is needed between first chamber 118 and second chamber 120. With no membrane, ions are free to migrate between cathode 114 and anode 116. Also, migrating ions and reactive products can collide and combine and react as needed when with a membrane these ions and products might not otherwise interact. In some embodiments, if a membrane is used, these ions and products can interact when the outputs of the first chamber 118 and second chamber 120 are combined.

Entry holes 142 into first chamber 118 can be fed from the same liquid source feeding entry holes 132 or from an independent source. Entry holes 142 can be located at the top or bottom of cell 100. In one embodiment, entry holes 142 can be located on bottom plate 106. In some embodiments, entry holes 142 can be located on the periphery of cell 100 embedded in circumferential body ring 104. Any number of entry ports 142 can be included in first chamber 118 that allow sufficient electrolysis of the target liquid. For example, one, two, three, four, five, six, seven, eight, nine, ten, eleven, twelve, 13, 14, 15, 16, 17, 18, 19, or 20 entry ports can be used.

Each cathode 114 can include an electrolytic cathode connection point 144. Electrolytic cathode connection point 144 can be configured to hook up to an appropriately charged power source.

Electrolyzed liquid can be removed from first chamber 118 from one or more output ports 146. Output ports 146 can be located or emanate from any surface on cell 100 that allows proper electrolysis. In one embodiment, output ports 146 can emanate through top plate 102. First chamber 118 can include any number of output ports 146 that allow for electrolyzed liquid to be removed as needed by the cell. For example, first chamber 118 can include two, three, four, five, six, seven, eight, nine, ten, eleven, twelve, 13, 14, 15, 16, 17, 18, 19, 20, or more output ports 146. In one embodiment, first chamber 118 can include three output ports 146. In another embodiment, first chamber 118 can include six output ports 146.

In one embodiment, output ports 146 from the first chamber 118 and the output ports 134 from the second chamber 120 can feed different product holding tanks. In another embodiment, output ports 146 from the first chamber 118 and output ports 134 from the second chamber 120 can feed the same product holding tank(s). In other words, in one embodiment, the product removed from first chamber 118 and the product from second chamber 120 can be mixed as a final product.

Output ports 146 from the first chamber 118 and the output ports 134 from the second chamber 120 can be of any variety of connection system that can allow transfer of liquids in and out of cell 100 without significant leakage. For example, output ports 146 and output ports 134 can be connected to plastic tubing, rubber tubing, glass tubing, or metal tubing. Connection types can include barb fittings, push fittings, crimp fittings, screw on fittings, quick release fittings, or the like formed of plastic, metal, rubber, or a combination thereof. Further, connections can include gaskets or o-rings as necessary to prevent leakage.

Flow rate through first chamber 118 can be any flow rate that allows sufficient electrolysis time to form a desired product. Flow rates through first chamber 118 can be about 0.5 gal/hr, about 1 gal/hr, about 5 gal/hr, about 10 gal/hr, about 15 gal/hr, about 20 gal/hr, about 30 gal/hr, about 40 gal/hr, about 50 gal/hr, about 60 gal/hr, about 70 gal/hr, about 80 gal/hr, about 90 gal/hr, about 100 gal/hr, about 200 gal/hr, about 300 gal/hr, about 400 gal/hr, about 500 gal/hr, about 600 gal/hr, about 700 gal/hr, about 800 gal/hr, about 900 gal/hr, about 1,000 gal/hr, about 1,100 gal/hr, about 1,200 gal/hr, about 1,300 gal/hr, about 1,400 gal/hr, about 1,500 gal/hr, about 1,600 gal/hr, about 1,700 gal/hr, about 1,800 gal/hr, about 1,900 gal/hr, about 2,000 gal/hr, about 2,100 gal/hr, about 2,200 gal/hr, about 2,300 gal/hr, about 2,400 gal/hr, about 2,500 gal/hr, or higher. In one embodiment, the flow rate can be about 20 gal/hr.

Flow rate through second chamber 120 can be any flow rate that allows sufficient electrolysis time to form a desired product. Flow rates through first chamber 118 can be 0.5 gal/hr, about 1 gal/hr, about 5 gal/hr, about 10 gal/hr, about 15 gal/hr, about 20 gal/hr, about 30 gal/hr, about 40 gal/hr, about 50 gal/hr, about 60 gal/hr, about 70 gal/hr, about 80 gal/hr, about 90 gal/hr, about 100 gal/hr, about 200 gal/hr, about 300 gal/hr, about 400 gal/hr, about 500 gal/hr, about 600 gal/hr, about 700 gal/hr, about 800 gal/hr, about 900 gal/hr, about 1,000 gal/hr, about 1,100 gal/hr, about 1,200 gal/hr, about 1,300 gal/hr, about 1,400 gal/hr, about 1,500 gal/hr, about 1,600 gal/hr, about 1,700 gal/hr, about 1,800 gal/hr, about 1,900 gal/hr, about 2,000 gal/hr, about 2,100 gal/hr, about 2,200 gal/hr, about 2,300 gal/hr, about 2,400 gal/hr, about 2,500 gal/hr, or higher. In one embodiment, the flow rate can be about 20 gal/hr.

Flow rates through first chamber 118 and second chamber 120 can be the same or can be different. In one embodiment, flow rate through first chamber 118 is faster than flow rate through second chamber 120. In some embodiments, each sub-chamber of second chamber 120 can have a different flow rate or can have the same flow rate. For example, if different products are desired from each sub-chamber, different flow rates can be used to produce different biologically reactive species.

Products from first chamber 118 and products from second chamber 120 can be mixed at a ratio of about 1:1. However, the two products may not need to be mixed in a 1:1 ratio. For example, ratios can be about 100:1, about 50:1, about 25:1, about 15:1, about 10:1, about 5:1, about 2:1, about 1:1, about 1:2, about 1:5, about 1:10, about 1:15, about 1:25, about 1:50, or about 1:100.

In one embodiment, output ports 134 can be combined into a product output location. In another embodiment, output ports 146 can be combined into a different product output location. In still another embodiment, output ports 134 and output ports 146 can be combined into a single product output location.

In one embodiment, each of first sub-chamber 122, second sub-chamber 124, and third sub-chamber 126 can be used to form a different product. Or, in other embodiments, two sub-chambers can be used to make one product and the other sub-chamber can be used to make a different product. In still other embodiments, more or fewer than three sub-chambers can be used. For example, if cell 100 includes 12 anodes, each anode can feed a separate sub-chamber giving 12 sub-chambers.

In another example embodiment, if each sub-chamber is used to make a different product, each product can be mixed or not mixed with the product from first chamber 118. If mixed with the product from chamber 118, each sub-chamber can be mixed at a desired ratio relative to each sub-chamber and also to the product from first chamber 118.

In some embodiments, anodes and cathodes can be physically switched thereby reversing relative polarity between the cathode and anode. In other embodiments, the polarity of the cathodes and anodes can simply be reversed. When switching anodes and cathodes, the cathodes can be formed with inputs in their surface and anodes may not include any inputs on their surface.

The same or a different voltage can be applied to each electrode or each sub-chamber depending on the desired end product. For example, a higher voltage can be applied to electrodes associated with one sub-chamber and a lower voltage to electrodes associated with a different sub-chamber.

When voltage is applied to the electrodes (e.g., anode 116 and cathode 114) electric fields between the electrodes can cause movement of ions. Negative ions can move toward an anode and positive ions toward a cathode. This can enable necessary exchange of reactants and products between the electrodes.

Any power supply can be used to provide energy to cell 100. In one embodiment, a power supply providing a modulating current can be used. In another embodiment, a power source with an AC ripple instead of the traditional DC source can be used. For example, electricity can enter from the wall and can be changed to a pulsing current with a rectifier. A single or half-wave rectifier can be used. Single or half-wave rectification can be a situation where either the positive or negative half of an AC wave is passed, and the other half is blocked. This can be done by using only one diode. In other words, the rectifier can create a current with a pulsating or spiking waveform. In other words, the voltage of the current can modulate from zero to a positive number many times per second. When the voltage goes down to 0V ions can drift apart/migrate and reorganize before the next increase in voltage. Spiking in voltage can allow for and/or promote a variable range of frequencies influencing many different types of compounds and/or ions. In one embodiment, the current is a rectified current.

Pulsing potentials in the power supply providing voltage to the anodes and cathodes can be provided. Lack of filter capacitors in a rectified power supply which can provide a pulsing potential can cause the voltages to drop to zero about 120 times per second, resulting in a hard spike when alternating current power lines change polarity. This hard spike, under Fourier Transform, can emit a large bandwidth of frequencies. In one embodiment, voltage can vary from high potential to zero about 120 times a second. In other embodiments, the voltage can vary from high potential to zero about 1,000 times a second, about 500 times a second, about 200 times a second, about 150 times a second, about 120 times a second, about 100 times a second, about 80 times a second, about 50 times a second, about 40 times a second, about 20 times a second, between about 200 times a second and about 20 times a second, between about 150 times a second and about 100 times a second, at least about 100 times a second, at least about 50 times a second, or at least about 120 times a second. This power modulation can allow the electrodes to sample all voltages and also provides enough frequency bandwidth to excite resonances in the forming molecules themselves. The time at very low voltages can also provide an environment of low electric fields where ions of similar charge can come within close proximity to the electrodes. All of these factors together can provide a possibility for the formation of stable complexes capable of generating and preserving free radicals.

Figure 6:
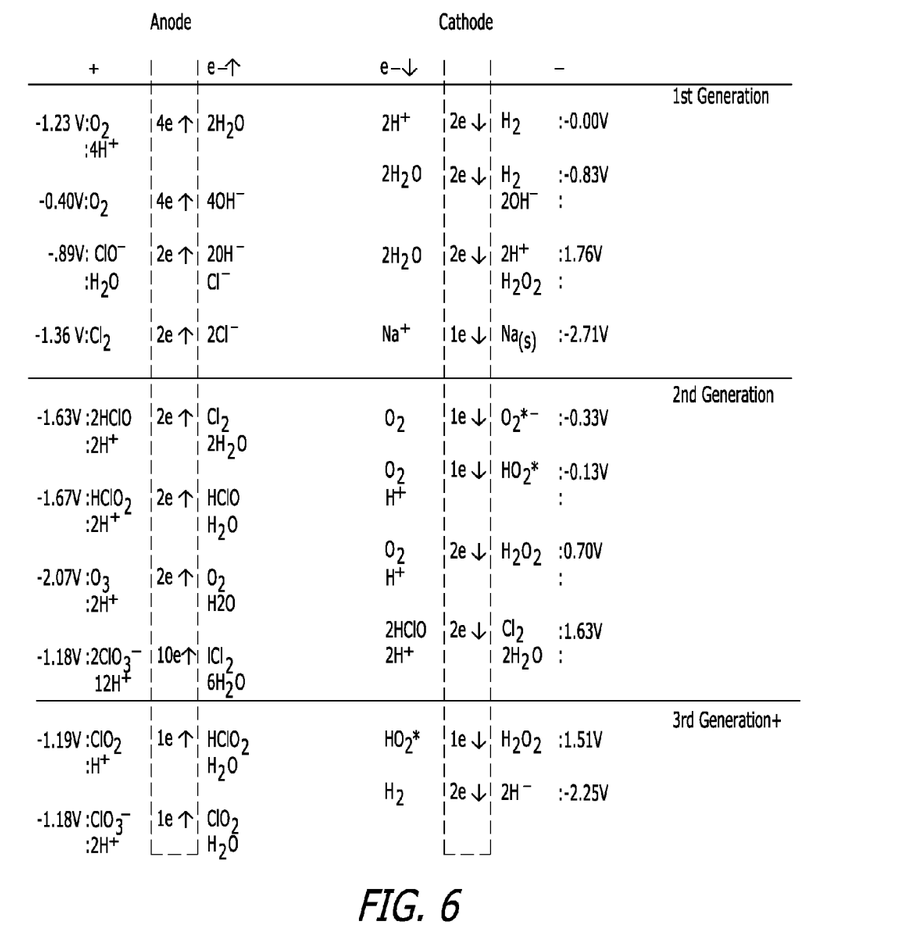
FIG. 6 illustrates an example generational diagram of various molecules at the electrodes.

FIG. 6 illustrates an example diagram of the generation of various molecules at the electrodes, the molecules written between the electrodes depict the initial reactants and those on the outside of the electrodes depict the molecules/ions produced at the electrodes and their electrode potentials. The diagram is broken into generations where each generation relies on the products of the subsequent generations.

The end products of this electrolytic process can react within the salinated solution to produce many different chemical entities. The compositions and beverage described herein can include one or more of these chemical entities. These end products can include, but are not limited to superoxides: $O_2^{*-}$, $HO_2^*$, hypochlorites: $OCl^-$, $HOCl$, $NaOCl$; hypochlorates: $HClO_2$, $ClO_2$, $HClO_3$, $HClO_4$; oxygen derivatives: $O_2$, $O_3$, $O_4^{*-}$, $1O$; hydrogen derivatives: $H_2$, $H^-$; hydrogen peroxide: $H_2O_2$; hydroxyl free Radical: $OH^{*-}$; ionic compounds: $Na^+$, $Cl^-$, $H^+$, $OH^-$, $NaCl$, $HCl$, $NaOH$; chlorine: $Cl_2$; and water clusters: $n*H_2O$ induced dipolar layers around ions.

After amperage has been run through the solution for a sufficient time, an electrolyzed solution can created with beneficial properties. The liquid emanating from first chamber 118 can have a relatively high pH of about 6.0, about 6.5, about 7.0, about 7.1, about 7.2, about 7.3, about 7.4, about 7.5, about 7.6, about 7.8, about 8.0, about 8.2, about 8.4, about 8.8, about 9.2, about 9.6, about 10, about 11, between about 7.2 and about 10, or between about 7.3 and 9.0. In one embodiment, the liquid emanating from first chamber 118 can have a neutral pH. The liquid emanating from second chamber 120 can have a relatively low pH of about 8.0, about 7.9, about 7.8, about 7.7, about 7.6, about 7.5, about 7.4, about 7.3, about 7.2, about 7.0, about 6.8, about 6.6, about 6.4, about 6.0, about 5.6, about 5.2, about 4, about 3, between about 7.6 and about 3, or between about 7.5 and 6.0. In one embodiment, the liquid emanating from second chamber 120 can have a neutral pH. As described, the liquid emanating from first chamber 118 and the liquid emanating from second chamber 120 can be combined. The resulting combined product can have a pH of about 6.0, about 6.5, about 7.0, about 7.1, about 7.2, about 7.3, about 7.4, about 7.5, about 7.6, about 7.8, about 7.9, about 8.0, about 8.1, about 8.2 about 8.3, about 8.4, between about 7.0 and about 7.8, or between about 7.2 and 7.6. In one embodiment, the pH of the combined product is neutral. In another embodiment, the pH is about 8.01. In some embodiments, the pH is greater than 7.4. In some embodiments, the pH is not acidic. In other embodiments, the solution can have a pH less than about 7.5. The pH may not be basic. The solution can be stored and or tested for particular properties.

In other embodiments, the pH of the liquids entering the apparatus, the liquids emanating there from, or the final products can be altered. For example, the pH of a solution can be increased using a base or decreased using an acid.

In some embodiments, substantially no organic material is present in the products described. Substantially no organic material can be less than about 0.1 ppt, less than about 0.01 ppt, less than about 0.001 ppt or less than about 0.0001 ppt of total organic material.

The chlorine concentration of a combined product can be about 5 ppm, about 10 ppm, about 15 ppm, about 20 ppm, about 21 ppm, about 22 ppm, about 23 ppm, about 24 ppm, about 25 ppm, about 26 ppm, about 27 ppm, about 28 ppm, about 29 ppm, about 30 ppm, about 31 ppm, about 32 ppm, about 33 ppm, about 34 ppm, about 35 ppm, about 36 ppm, about 37 ppm, about 38 ppm, less than about 38 ppm, less than about 35 ppm, less than about 32 ppm, less than about 28 ppm, less than about 24 ppm, less than about 20 ppm, less than about 16 ppm, less than about 12 ppm, less than about 5 ppm, between about 30 ppm and about 34 ppm, between about 28 ppm and about 36 ppm, between about 26 ppm and about 38 ppm, between about 20 ppm and about 38 ppm, between about 5 ppm and about 34 ppm, between about 10 ppm and about 34 ppm, or between about 15 ppm and about 34 ppm. In one embodiment, the chlorine concentration is about 32 ppm. In another embodiment, the chlorine concentration is less than about 41 ppm.

The saline concentration of the combined product can be about 0.10% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.20% w/v, about 0.30% w/v, about 0.40% w/v, about 0.50% w/v, about 0.60% w/v, about 0.70% w/v, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The combined product generally can include electrolytic and/or catalytic products of pure saline that mimic redox signaling molecular compositions of the native salt water compounds found in and around human cells. The product can be fine tuned to mimic or mirror molecular compositions of different biological media. The product can have reactive species other than chlorine present. As described, species present in the products and beverages described herein can include, but are not limited to $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O$, $OH^{*-}$, $HOCl-O_2^{*-}$, $HOCl-O_3$, $O_2^{*-}$, $HO_2^*$, $NaCl$, $HCl$, $NaOH$, and water clusters: $n*H_2O$-induced dipolar layers around ions, several variations.

In one embodiment, the product can include $OCl^-$, $HOCl$, $NaOCl$, $HClO_2$, $ClO_2$, $HClO_3$, $HClO_4$, $H_2O_2$, $H^+$, $H^-$, $OH^-$, $O_3$, $O_4^{*-}$, $^1O$, $OH^{*-}$, $HOCl-O_2^{*-}$, $HOCl-O_3$, $O_2^{*-}$, and $HO_2^*$.

In one embodiment, the product can include $OCl^-$; $ClO_2$, $HClO_3$, $HClO_4$, $H_2O_2$, $H^+$, $H^-$, $OH^-$, $O_3$, $O_4^{*-}$, $^1O$, $OH^{*-}$; $HOCl-O_2^{*-}$, $HOCl-O_3$, $O_2^{*-}$, and $HO_2^*$.

In one embodiment, the product can include $OCl^-$, $ClO_2$, $H_2O_2$, $H^+$, $H^-$, $OH^-$, $O_3$, $O_4^{*-}$, $^1O$, $OH^{*-}$, $HOCl-O_2^{*-}$, $HOCl-O_3$, $O_2^{*-}$, and $HO_2^*$.

In one embodiment, the product can include $OCl^-$, $OH^-$, $O_3$, $O_4^{*-}$, $OH^{*-}$, $HOCl-O_2^{*-}$, $HOCl-O_3$, $O_2^{*-}$, and $HO_2^*$.

In one embodiment, the product can include $OCl^-$, $O_3$, $O_4^{*-}$, $OH^{*-}$, $HOCl-O_2^{*-}$, $HOCl-O_3$, and $O_2^{*-}$.

In one embodiment, the product can include $O_4^{*-}$, $OH^{*-}$, $HOCl-O_2^{*-}$, $O_2^{*-}$, and $HO_2^*$.

In one embodiment, the product can include $O_2^{*-}$, and $HO_2^*$.

In one embodiment, the product can include stabilized $O_2^{*-}$.

In one embodiment, the product can include $OCl^-$, $H^-$, $OH^-$, $O_4^{*-}$, $^1O$, $OH^{*-}$, $HOCl-O_2^{*-}$, $O_2^{*-}$, and $HO_2^*$.

Depending on the parameters used make the product, different components can be present at different concentrations. In one embodiment, the product can include about 0.1 ppt, about 0.5 ppt, about 1 ppt, about 1.5 ppt, about 2 ppt, about 2.5 ppt, about 3 ppt, about 3.5 ppt, about 4 ppt, about 4.5 ppt, about 5 ppt, about 6 ppt, about 7 ppt, about 8 ppt, about 9 ppt, about 10 ppt, about 20 ppt, about 50 ppt, about 100 ppt, about 200 ppt, about 400 ppt, about 1,000 ppt, between about 0.1 ppt and about 1,000 ppt, between about 0.1 ppt and about 100 ppt, between about 0.1 ppt and about 10 ppt, between about 2 ppt and about 4 ppt, at least about 0.1 ppt, at least about 2 ppt, at least about 3 ppt, at most about 10 ppt, or at most about 100 ppt of $OCl^-$. In some embodiments, $OCl^-$ can be present at about 3 ppt. In other embodiments, $OCl^-$ can be the predominant chlorine containing species in the beverage.

In some embodiments, hydroxyl radicals can be stabilized in the product by the formation of radical complexes. The radical complexes can be held together by hydrogen bonding. Another radical that can be present in the product is an OOH. radical. Still other radical complexes can include a nitroxyl-peroxide radical (HNO—HOO*) and/or a hypochlorite-peroxide radical (HOCl—HOO*).

In one embodiment, the products can include HNO—HOO*.

In one embodiment, the products can include HOCl—HOO*.

In one embodiment, the products can include HNO—HOO* and HOCl—HOO*.

Reactive species' concentrations in the product, detected by fluorescence photo spectroscopy, may not significantly decrease in time. Bound HOCl—$*O_2^-$ complexes are possible at room temperature. Molecular complexes can preserve volatile components of reactive species. For example, reactive species concentrations in whole blood as a result of molecular complexes may prevent reactive species degradation over time.

In one embodiment, the products include HOCl—$*O_2^-$.

In one embodiment, the products can include NHO—HOO*, HOCl—HOO*, and HOCl—$*O_2^-$.

Reactive species and biologically reactive species can be further divided into "reduced species" (RS) and ROS. Reactive species can be formed from water molecules and chloride salt ions when restructured through a process of forced electron donation. Electrons from lower molecular energy configurations in the salinated water may be forced into higher, more reactive molecular configurations. The species from which the electron was taken can be "electron hungry" and is called the RS and can readily become an electron acceptor (or proton donor) under the right conditions. The species that obtains the high-energy electron can be an electron donor and is called the ROS and may energetically release these electrons under the right conditions.

The products can be life enhancing beverages and can be stored and bottled as needed to ship to consumers. The life enhancing beverage can have a shelf life of about 5 days, about 30 days, about 3 months, about 6 months, about 9 months, about 1 year, about 1.5 years, about 2 years, about 3 years, about 5 years, about 10 years, at least about 5 days, at least about 30 days, at least about 3 months, at least about 6 months, at least about 9 months, at least about 1 year, at least about 1.5 years, at least about 2 years, at least about 3 years, at least about 5 years, at least about 10 years, between about 5 days and about 1 year, between about 5 days and about 2 years, between about 1 year and about 5 years, between about 90 days and about 3 years, between about 90 days and about 5 year, or between about 1 year and about 3 years.

The life enhancing beverage can be bottled in plastic bottles having volumes of about 4 oz, about 8 oz, about 16 oz, about 32 oz, about 48 oz, about 64 oz, about 80 oz, about 96 oz, about 112 oz, about 128 oz, about 144 oz, about 160 oz, or any range created using any of these values. The plastic bottles can also be plastic squeezable pouches having similar volumes. In one embodiment, plastic squeezable pouches can have one way valves to prevent leakage of the life enhancing beverage, for example, during athletic activity.

During bottling, solution from an approved batch can be pumped through a 10 micron filter (e.g., polypropylene) to remove any larger particles from tanks, dust, hair, etc. that might have found their way into the batch. In other embodiments, this filter need not be used. Then, the solution can be pumped into the bottles, the overflow going back into the batch.

Bottles generally may not contain any dyes, metal specks or chemicals that can be dissolved by acids or oxidating agents. The bottles, caps, bottling filters, valves, lines and heads used can be specifically rated for acids and oxidating agents. Caps and with organic glues, seals or other components sensitive to oxidation may be avoided, as these could neutralize and weaken the product over time.

The bottles and pouches used herein can aid in preventing decay of free radical species found within the beverages. In other embodiments, the bottles and pouches described do not further the decay process. In other words, the bottles and pouches used can be inert with respect to the radical species in the beverages. In one embodiment, a container (e.g., bottle and/or pouch) can allow less than about 10% decay/month, less than about 9% decay/month, less than about 8% decay/month, less than about 7% decay/month, less than about 6% decay/month, less than about 5% decay/month, less than about 4% decay/month, less than about 3% decay/month, less than about 2% decay/month, less than about 1% decay/month, between about 10% decay/month and about 1% decay/month, between about 5% decay/month and about 1% decay/month, about 10% decay/month, about 9% decay/month, about 8% decay/month, about 7% decay/month, about 6% decay/month, about 5% decay/month, about 4% decay/month, about 3% decay/month, about 2% decay/month, or about 1% decay/month of free radicals in the beverage. In one embodiment, a bottle can only result in about 3% decay/month of superoxide. In another embodiment, a pouch can only result in about 4% decay/month of superoxide.

Quality Assurance testing can be done on every batch before the batch can be approved for bottling or can be performed during or after bottling. A 16 oz. sample bottle can be taken from each complete batch and analyzed. Determinations for presence of contaminants such as heavy metals or chlorates can be performed. Then pH, free chlorine, and total chlorine concentrations and reactive molecule concentrations of the active ingredients can be analyzed by fluorospectroscopy methods. These results can be compared to those of a standard solution which is also tested along side every sample. If the results for the batch fall within a certain range relative to the standard solution, it can be approved. A chemical chromospectroscopic MS analysis can also be run on random samples to determine if contaminants from the production process are present.

The beverage can be consumed by ingestion. In other embodiments, the beverage can be provided as a solution for injection. In some embodiments, injection can be subcutaneous, intra-luminal, site specific (e.g., injected into a cancer or internal lesion), or intramuscular. Intravenous injection can also be desirable. The life enhancing solution can be packaged in plastic medical solution pouches having volumes of about 4 oz, about 8 oz, about 16 oz, about 32 oz, about 48 oz, about 64 oz, about 80 oz, about 96 oz, about 112 oz, about 128 oz, about 144 oz, about 160 oz, or any range created using any of these values, and these pouches can be used with common intravenous administration systems.

In other embodiments, administration can be oral, parenteral, topical, systemic, intraocular, subcutaneous, intramuscular, intraobrital, intracapsular, intraspinal, intrasternal, or the like, a combination thereof, or any other route known in the art.

In one embodiment, any number of cells 100 can be linked together to allow a higher volume of salinated water to be electrolyzed. For example, two, three, four, five, six, seven, eight, nine, ten, eleven, twelve, 13, 14, 15, 16, 17, 18, 19, 20, 25, 30, 35, 40, 45, 50, 60, 70, 80, 90, 100, 125, 150, 175, 200, or more cells can be linked. In one embodiment, at least two, at least three, at least four, at least five, at least ten, at least 20, at least 30, at least 40, or at least 50, cells can be linked. Cells can be linked together in series or parallel.

In some embodiments, if linked, salinated water, electrolyzed water or both can be chilled between each cell, between every other cell, between every third cell, between every fourth cell, between every fifth cell, between every sixth cell, between every seventh cell, between every eighth cell, between every ninth cell, between every tenth cell, or between any number of cells as appropriate to generate a particular set of constituents in the electrolyzed water. In one embodiment, water can be chilled after each cycle through a set of linked cells.

Also, if linked, the output of one cell can be the input of the next cell. In other words, if ten cells are linked, liquid would sequentially travel from cell one down the line to cell ten. In another embodiment, the output from the first chamber can be mixed with the output of the second chamber between each cell in a series.

Methods of electrolyzing salinated water and forming the products described herein are described. These methods comprise supplying a first salinated water stream to first chamber 118 including at least one cathode 114 configured to electrolyze a first salinated water stream entering first chamber 118 and creating a high pH product. Also included in the method is a step of supplying a second salinated water stream to second chamber 120 including at least one anode 116 configured to electrolyze the second salinated water stream entering second chamber 120 and creating a low pH product. A voltage can be applied between the cathode 118 and anode 116 to electrolyze the first salinated water stream and the second salinated water stream while providing a membrane 140 separating the first chamber 118 and the second chamber 120. Membrane 140 can be configured to prevent water to pass between the first chamber 118 and the second chamber 120 yet allow ions to pass through. In some embodiments, the second chamber 120 includes an inlet 132 in the anode 116 and the second salinated water stream resides within at most 5 inches of a surface of the anode 116 for at least 1 second to electrolyze the second salinated water stream. In some embodiments, the high pH product and the low pH product are combined to make a final product.

Example 1

Described here is an example process of forming a life enhancing beverage or product using the apparatus and systems described herein. One skilled in the art understands that changes can be made to the system to alter the life enhancing beverage, and these changes are within the scope of the present description.

Incoming water can be subjected to reverse osmosis system at a temperature of about 15-20° C. to achieve purified water with about 8 ppm of total dissolves solids. Purified water, is then fed at a temperature of about 15-20° C. into distiller and processed to achieve distilled water with about 0.5 ppm of total dissolved solids.

A system to produce a product can include a water source which can feed directly into a carbon filter. After oils, alcohols, and other volatile chemical residuals and particulates are removed by carbon filter, the water can be directed to resin beds within a water softener which can remove dissolved minerals. Then, as described above, the water can pass through reverse osmosis system and distiller.

As needed, distilled water can be gravity fed from tank into a saline storage tank. A handheld meter can be used to test distilled water for salinity.

Saline storage tank is then salted using a brine system. The brine tank is filled with distilled water and then NaCl is added to the brine tank at a ratio of about 537.5 g/gal of liquid. At this point, the water is circulated in the brine tank for about 4 days.

Prior to addition of brine to a handling tank, the salinity of the water in can be tested using a handheld conductivity meter such as an YSI ECOSENSE® ecp300 (YSI Inc., Yellow Springs, Ohio). Any corrections based on the salinity measurements can be made at this point. Brine solution is then added to the handling tank to achieve a salt concentration of about 10.75 g/gal. The salted water is circulated in handling tank at a rate of about 100 gal/hr for no less than about 72 hr. This circulation is performed at room temperature. A handheld probe can again be used to test salinity of the salinated solution. In one embodiment, the salinity is about 2.8 ppth.

In one example method for filling and mixing the salt water in the brine holding tank, the amount of liquid remaining in the tank is measured. The amount of liquid remaining in a tank is measured by recording the height that the liquid level is from the floor that sustains the tank, in centimeters, and referencing the number of gallons this height represents. This can be done from the outside of the tank if the tank is semi-transparent. Then, after ensuring that the output valve is closed, distilled water can be pumped in. The amount of distilled water that is being pumped into a holding tank can then be calculated by measuring the rise in liquid level: subtracting the initial height from the filled height and then multiplying this difference by a known factor.

The amount of salt to be added to the tank is then calculated by multiplying 11 grams of salt for every gallon of distilled water that has been added to the tank. The salt can be carefully weighed out and dumped into the tank.

The tank is then agitated by turning on the recirculation pump and then opening the top and bottom valves on the tank. Liquid is pumped from the bottom of the tank to the top. The tank can be agitated for three days before it may be ready to be processed.

After agitating the tank for more than 6 hours, the salinity is checked with a salinity meter by taking a sample from the tank and testing it. Salt or water can be added to adjust the salinity. If either more water or more salt is added then the tank is agitated for 6 more hours and tested again. After about three days of agitation, the tank is ready to be processed.

Salinated water is then chilled. A chiller is used to cool heat exchangers to about 0-5° C. The salinated water is circulated through the heat exchangers which are circulated with propylene glycol until the temperature of the salinated water is about 4.5-5.8° C.

The chill salinated water is then transferred into a device described herein. Each device includes 24 electrodes (12 cathodes and 12 anodes). Electrodes can be cylindrical structures formed of titanium and plated with platinum. Electrochemical processing of the cold salinated water can be run using a continuous flow of water at a rate of about 20 gal/hr through the first and the second chambers. A rectified current power supply is used to power the electrodes at less than or about 30V. In one embodiment, a membrane between first chamber and second chamber is not needed. In another embodiment, a membrane is used.

An independent current meter can be used to set the current.

The flow out of the device can be collected or run through subsequent devices. When collected, the output from the first chamber and the second chamber can be combined. After combination, life enhancing water has been created with a pH of about 7.4, 32 ppm of chlorine, 100% $OCl^-$ and 100% $O^{-2}$. Life enhancing water is transferred to storage tanks where the life enhancing water awaits bottling where it is shipped to consumers as a life enhancing beverage.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An electrolyzing system comprising:
   a first chamber including at least one cathode configured to electrolyze a first salinated water stream and create a high pH product;
   a second chamber including at least one anode configured to electrolyze a second salinated water stream and create a low pH product, the second chamber including
      an electrolytic volume, the at least one anode positioned within the electrolytic volume,
      an input port fluidly connected to the electrolytic volume,
      an overflow port positioned proximal a top end of the electrolytic volume,
      a sub-chamber fluidly connected to the electrolytic volume by the overflow port, and
      an output port configured to allow outflow from the sub-chamber of the second chamber; and
   a membrane between the first chamber and the second chamber configured to allow ions through and prevent water from passing,
   wherein the electrolytic volume of the second chamber is configured in size and shape such that the second salinated water stream resides within at most 5 inches of a surface of the anode for at least 1 second to electrolyze the second salinated water stream before passing through the overflow port into the sub-chamber of the second chamber.

2. The electrolyzing system of claim 1, wherein the cathode, the anode, or the cathode and the anode are driven with 30V of power.

3. The electrolyzing system of claim 1, wherein the at least one anode is cylindrical and a cylindrical chamber surrounds the at least one anode.

4. The electrolyzing system of claim 1, wherein the first salinated water stream flows through first chamber at a rate of about 20 gal/hr.

5. The electrolyzing system of claim 1, wherein the second salinated water stream flows through second chamber at a rate of about 20 gal/hr.

6. The electrolyzing system of claim 1, wherein the first salinated water stream and the second salinated water stream are chilled to a temperature of about 5° C.

7. The electrolyzing system of claim 1, wherein the second chamber further comprises a second sub-chamber, and a third sub-chamber.

8. The electrolyzing system of claim 7, wherein the sub-chamber, the second sub-chamber, and the third sub-chamber have substantially similar volumes.

9. The electrolyzing system of claim 8, wherein each of the sub-chamber, the second sub-chamber, and the third sub-chamber includes four anodes.

10. The electrolyzing system of claim 1, wherein the first chamber includes 12 cathodes.

11. The electrolyzing system of claim 1, wherein a distance between the anode and the cathode is between about ½ in and about 2 in.

12. The electrolyzing system of claim 1, wherein the anode comprises:
    a hollow interior region fluidly connected to the input port; and
    at least one entry hole fluidly connected the hollow interior region to the first volume of the second chamber.

13. The electrolyzing system of claim 12, wherein the at least one entry hole is configured to dictate the flow of the second salinated water stream within the electrolytic volume.

14. The electrolyzing system of claim 13, wherein the at least one entry hole is configured to create a vortex within the electrolytic volume.

* * * * *